United States Patent [19]

Thoemel et al.

[11] Patent Number: 4,665,221

[45] Date of Patent: May 12, 1987

[54] PREPARATION OF TERPENOID FORMATES

[75] Inventors: Frank Thoemel, Weinheim; Werner Hoffmann, Neuhofen, both of Fed. Rep. of Germany

[73] Assignee: BASF Aktiengesellschaft, Fed. Rep. of Germany

[21] Appl. No.: 516,854

[22] Filed: Jul. 25, 1983

Related U.S. Application Data

[63] Continuation of Ser. No. 325,771, Nov. 30, 1981, abandoned, which is a continuation of Ser. No. 30,854, Apr. 17, 1979, abandoned.

[30] Foreign Application Priority Data

Apr. 26, 1978 [DE] Fed. Rep. of Germany ....... 2818150

[51] Int. Cl.$^4$ .................... C07C 67/08; C07C 67/293; C07C 69/07
[52] U.S. Cl. .................................. 560/249; 560/237; 560/248; 562/609; 568/875; 570/189; 570/217
[58] Field of Search ................ 560/249, 261; 568/877, 568/875

[56] References Cited

U.S. PATENT DOCUMENTS

| | | | |
|---|---|---|---|
| 2,902,510 | 9/1959 | Webb | 560/249 |
| 2,935,526 | 5/1960 | Bain | 560/249 |
| 3,927,076 | 12/1975 | Babler | 560/261 |

FOREIGN PATENT DOCUMENTS

| | | |
|---|---|---|
| 80711 | 2/1893 | Fed. Rep. of Germany . |
| 2459546 | 7/1975 | Fed. Rep. of Germany . |
| 2513198 | 10/1975 | Fed. Rep. of Germany . |
| 2509967 | 9/1976 | Fed. Rep. of Germany ...... 560/261 |
| 765516 | 1/1957 | United Kingdom ................ 560/249 |
| 1445069 | 8/1976 | United Kingdom . |
| 1529592 | 10/1978 | United Kingdom ................ 560/249 |

OTHER PUBLICATIONS

Helv. Chim. Acta, 8(1925) pp. 269-274 Ibid., 26(1943), pp. 1741-1750.
Annalen, 475(1929), pp. 183-204.
J. für Prakt. Chem., 45, 1892, p. 601.
Berichte, 39, 1906, pp. 1780-1792.
Chemie für Labor und Betrieb, 28, 1977, p. 171.

*Primary Examiner*—Vivian Garner
*Attorney, Agent, or Firm*—Keil & Weinkauf

[57] ABSTRACT

An improved process for the preparation of primary terpenoid alcohols, e.g. 6,7-dihydrogeraniol and phytol, and of their esters with formic acid. The terpenoid formates are obtained very advantageously by reacting the corresponding tert.-vinylcarbinols with more than 2 moles, per mole of vinylcarbinol, of aqueous formic acid of more than 70 percent strength by weight, or with anhydrous formic acid, at from 5° to 100° C. The primary terpenoid alcohols themselves are obtained from their formates by trans-esterification with a low-boiling alcohol in the presence of a catalytic amount of a strong base. The products are valuable compounds. For example, 6,7-dihydrogeraniol is used as a scent and phytol is used as a perfume fixative and as a starting material for the synthesis of naturally occurring materials.

1 Claim, No Drawings

PREPARATION OF TERPENOID FORMATES

This is a continuation of Ser. No. 325,771, filed Nov. 30, 1981, now abandoned, which is a continuation of Ser. No. 30,854, filed Apr. 17, 1979, now abandoned.

The present invention relates to an improved process for the preparation of terpenoid compounds of the general formula I

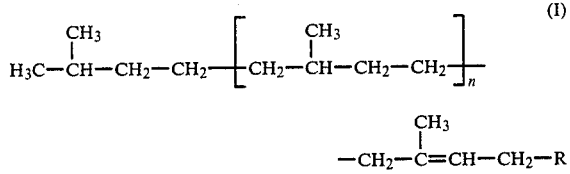

where R is

or —OH and n is 0, 1, 2 or 3, by reacting the corresponding tertiary vinylcarbinols with formic acid and thereafter, if desired, hydrolytically cleaving the ester group.

The terpenoid carbinols of the formula I are sought-after compounds. For example, 6,7-dihydrogeraniol (I, with n=0) is used as a scent and phytol (I, with n=2) is used as a perfume fixative and as a starting material for the synthesis of naturally occurring materials (for example, vitamin E is synthesized from phytol and trimethylhydroquinone).

Hitherto, the terpenoid carbinols of the formula I were in general obtained by reacting the corresponding tertiary vinylcarbinols of the general formula II

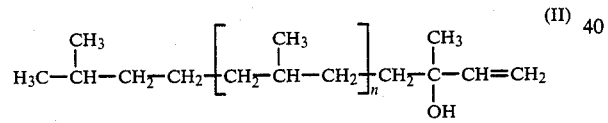

where n has the above meaning, with phosphorus halides, in a reaction accompanied by rearrangement to give the corresponding primary unsaturated halides of the formula III

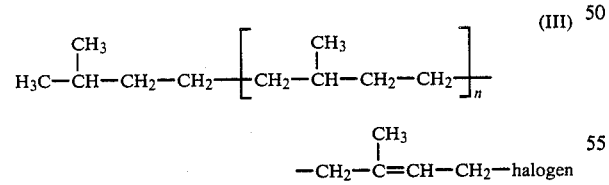

(halogen=chlorine or bromine) and, in a further step, converting these, by reaction with sodium acetate or potassium acetate, to the corresponding acetic acid esters, from which the terpenoid carbinols can be obtained by saponification with an alkali metal hydroxide solution. For example, phytol (P. Karrer et al., Helv. Chim. Acta 26 (1943), 1,741) and tetrahydrofarnesol (F. G. Fischer and K. Löwenberg, Annalen 475, (1929), 183) were prepared in this manner.

It is also known that tert.-vinylcarbinols can be converted directly, by means of acetic anhydride or acetic acid in the presence of acid catalysts, to the primary unsaturated acetates (German Laid-Open Application DOS 2,459,546 and German Pat. No. 80,711). Our own experiments on the reaction of isophytol with acetic anhydride in the presence of an acid catalyst have however shown that in addition to the desired acetate phytadiene is also produced. Because of its emulsifying properties, phytadiene, even in low concentrations, causes the formation of emulsions, which are difficult to break, during conventional working up of the reaction product obtained from the above process.

If a tert.-vinylcarbinol is allowed to react with acetic anhydride in the absence of an acid catalyst, the desired acetates of the unsaturated primary carbinols are only obtained in yields not exceeding 50% even after reaction times of more than 90 hours and using reaction temperatures of above 100° C. (F. G. Fischer and K. Löwenberg, Annalen 475 (1929), 183). Under these reaction conditions, a substantial proportion of diolefin is formed from the tert-vinylcarbinol. According to the above publication, only hydrocarbons are obtained if formic acid is used as the reagent (cf. loc. cit., page 192).

It is an object of the present invention to provide a process by means of which the terpenoid carbinols of the formula I can be obtained simply and in good yield, with cheap auxiliaries, from the tertiary vinylcarbinols of the formula II. German Laid-Open Application DOS 2,513,198 describes the rearrangement of isophytyl acetate to phytyl acetate in the presence of bis-(benzonitrile)-palladium chloride. However, this process is not very economical, because of the use of the expensive palladium complex as the catalyst. Furthermore, the direct conversion of isophytol, a cheap compound, to phytyl acetate is not achieved; to prepare the latter, isophytol must first be esterified.

We have found that the above object is achieved and that terpenoid compounds of the general formula I

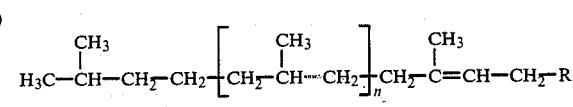

where R is —O—CO—H (Ia) or —OH (Ib) and n is 0, 1, 2 or 3 can be prepared by a process wherein A. the corresponding tert.-vinylcarbinol of the general formula II

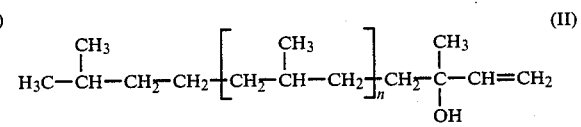

where n has the above meaning is reacted with more than 2 moles, per mole of vinylcarbinol, of formic acid which is in the form of an aqueous solution of more than 70 percent strength by weight or is anhydrous, at from 5° to 100° C., preferably from 30° to 80° C., and B. if R is OH, the terpenoid formate obtained in A is trans-esterified with a low-boiling alcohol in the presence of a catalytic amount of a strong base.

In a particularly advantageous embodiment of the process of the invention, the tertiary vinylcarbinol of the formula II is reacted, in step A, with aqueous formic acid of from 70 to 95 percent strength by weight, preferably from 80 to 90 percent strength by weight, at from 8°-100° C., preferably from 30° to 80° C., and the reaction is stopped virtually immediately when all the vinylcarbinol employed has been converted.

In a further advantageous embodiment of the process according to the invention, the tertiary vinylcarbinol of the formula II is reacted, in step A, with aqueous formic acid of more than 95 percent strength by weight or with anhydrous formic acid at from 5° to 80° C., preferably from 30° to 70° C., and the reaction is stopped virtually immediately when all the vinylcarbinol employed has been converted.

In a further very advantageous embodiment of the process according to the invention, the resulting terpenoid formate is trans-esterified, in step B, with methanol in the presence of a catalytic amount of an alkali metal methylate, the resulting methylformate being distilled off continuously.

Using the process according to the invention it is possible, by reacting a vinylcarbinol of the formula II with formic acid, to obtain the formate of the formula I in virtually quantitative yield; the formate can then, without special working-up, be converted, in very good yield, to the carbinol of the formula I by trans-esterification.

Accordingly, the process of the invention offers the possibility, starting from the tertiary vinylcarbinol, of obtaining the primary carbinol in what is virtually a one-vessel reaction, and in yields of from about 70 to 90% of theory.

This extremely advantageous result was very surprising.

The process according to the invention is remarkable inasmuch as F. G. Fischer and K. Löwenberg, Annalen 475 (1929), 192, have stated that in reacting tetrahydroneroilidol with formic acid to prepare tetrahydrofarnesol—admittedly under process conditions not specified in detail—exclusively hydrocarbons are formed.

The reactions, described in the literature, of tertiary vinylcarbinols with olefinically unsaturated hydrocarbon radicals in the presence of formic acid in order to prepare the corresponding primary carbinol formates, also did not lead to the expectation of the result achieved according to the invention, since the formates of the corresponding primary carbinols are in every case only obtained in low yield in a product mixture containing principally cyclic compounds or unsaturated hydrocarbons (cf. J. Bertram and H. Walbaum, J. für prakt. Chem. 45, (1892), 601; O. Zeitschel, Perichte 39, (1906), 1,780; L. Ruzicka and E. Carpato. Helv. Chim. Acta 8, (1925), 269).

The tertiary vinylcarbinols of the general formula II required as starting materials for the process according to the invention are known compounds which are readily obtainable, even on an industrial scale, from simple starting materials (cf. F. G. Fischer and K. Löwenberg, Annalen 475 (1929); P. Karrer et al., Helv. Chim. Acta 26 (1943), 1,741; A Nürrenbach, Chemie für Labor und Betrieb 28, (1977), 171).

The conversion, according to the invention, of a vinycarbinol II to a formate of the formula I is most advantageously carried out with aqueous formic acid of about 90% strength at from 55° to 65° C. Using the process according to the invention, it is not necessary to use an acid or Lewis acid as the catalyst of the trans-esterification which is accomplished by rearrangement.

The formic acid is in general used in from 2-fold to 100-fold molar excess, preferably in about 10-fold molar excess. If less than 2 moles of formic acid are used, the reaction cannot proceed to completion; conversely, more than 20 moles of formic acid per mole of vinylcarbinol in general provides no substantial further advantage.

If relatively concentrated formic acid, i.e., for example, formic acid containing less than 10% by weight of water, is employed, the undesired dienes are increasingly formed from the tertiary vinylcarbinols. Accordingly, the more concentrated the formic acid, the milder must be the reaction conditions chosen, i.e. the lower must be the reaction temperatures and/or the shorter must be the reaction times. For example, in reacting isophytol with 96% strength aqueous formic acid at from 60° to 70° C.; all the isophytol has already been converted after 10 minutes, so that extending the reaction time would only serve to increase the proportion of phytadiene in the reaction product. On the other hand, when using aqueous formic acid of about 90 percent strength by weight at 60°–70° C., reaction times of about 1–2 hours are advantageous. If the concentration of formic acid is further reduced, the reaction times required increase drastically. For example, if isophytol is reacted with about 10 moles of formic acid at 60° C., the use of formic acid of about 83 percent strength by weight requires a reaction time of more than 8 hours, and the use of formic acid of 77 percent strength by weight requires a reaction time of about 30 hours. The presence of more than 25% by weight of water in the formic acid results in disadvantageously long reaction times and in incomplete conversion of the vinylcarbinol II.

The reaction according to the invention is advantageously carried out at below 100° C. i.e. the maximum temperature should be somewhat below the boiling point of the excess formic acid, and is preferably from 30° to 80° C. and especially from 55° to 65° C. Below 30° C. disadvantageously long reaction times are needed. At higher reaction temperatures, i.e. at above 70° C., by-products are increasingly formed. In particular, the dienes are produced from the tert.-vinylcarbinols. The optimum reaction conditions for each particular tert.-vinylcarbinol of the general formula II differ, within the stated limits. For example, for isophytol, and when using about 90 percent strength by weight aqueous formic acid, it is particularly advantageous to heat the reaction mixture for 2 hours at about 60° C. For the conversion of tetrahydronerolidol to tetrahydrofarnesyl formate it is particularly advantageous to use aqueous formic acid of about 90 percent strength by weight and to heat the reaction mixture for about 1.25 hours at about 60° C.

The reaction can be carried out in a simple manner in glass or enamel vessels. The reactants are mixed and brought to the reaction temperature, whilst stirring. When the reaction has ended, the aqueous formic acid rapidly and cleanly separates out, as a lower phase, from the formate obtained. The recovered aqueous formic acid can be used for subsequent preparations and can be repeatedly restored to the required concentration by adding concentrated formic acid.

The formates separated off as crude products can be freed from residual dissolved formic acid by heating to at most 100° C. under greatly reduced pressure. They can subsequently be purified by distillation or be directly converted further to the alcohols of the formula I.

For the latter purpose, a purified formate of the formula I, or, advantageously, the crude formate which has merely been freed from residual formic acid, is mixed with an excess of a low-boiling alcohol, i.e. a $C_1$-$C_2$alkanol, preferably methanol, a small amount of a basic catalyst is added, and the reaction mixture is refluxed. Examples of suitable basic catalysts are alkali metal alcoholates, sodium hydroxide and potassium carbonate. The use of an alkali metal alkylate, especially of the cheap product sodium methylate, is preferred. Whilst heating the formate with the lower alcohol in the presence of the base, the resulting formic acid ester of the lower alcohol is in general distilled off slowly. The residue left consists of the carbinol of the general formula I, which is obtained, by this method, in a yield of from 70% to 90% of theory. Our own experiments show that the carbinols of the general formula I are obtained in yields of only about 50% if their esters are saponified with an alkali metal hydroxide solution instead of being trans-esterified with a lower alcohol.

Accordingly, the process of the invention provides a method of preparing the sought-after primary carbinols of the formula I in very good yield, and in virtually a one-vessel reaction, from the tertiary vinylcarbinols of the formula II. Some of the carbinols of the formula I are sought-after scents and fixatives, or starting materials for the synthesis of naturally occurring compounds.

EXAMPLES 1 to 8

Isophytol (formula II, with n=2) and formic acid are mixed, and the mixture is stirred at the reaction temperature in a glass or glass-lined steel reaction vessel which can be heated and cooled and is fitted with a stirrer and a short column.

The data relating to the amounts of isophytol and formic acid employed, the concentration of the formic acid used, the reaction time and the reaction temperature are listed in Table 1 below.

After the reaction, the lower phase which separated out and which consisted of aqueous formic acid was in each case removed. In Experiments 2 to 4, the aqueous formic acid recovered from the preceding experiment was in each case re-used as a standard amount. The crude phytyl formate obtained was heated at 100° C. under 15 mm Hg in order to distill off any formic acid still present (about 1–2% by weight). The phytyl formate thus obtained can be directly trans-esterified or can, if necessary, be purified by distillation. The content of phytyl formate and formic acid was determined by titration. All reactions were followed by thin layer chromatography (Merck prepared silica gel plates; migrating agent—3:1 mixture of cyclohexane and ethyl acetate; spray developer—$KMnO_4$ in concentrated $H_2SO_4$) and were, as far as possible, stopped when the isophytol had been completely converted.

The boiling point of the phytyl formate obtained was 160°–162° C./3 mbar (typical data according to U.S. Pat. No. 2,638,176:145°–155° C./0.1 mbar, $n_D^{25} = 1.4540$).

Table 1 lists the results achieved.

TABLE 1

| Example | | 1 | 2 | 3 | 4 | 5 | 6 | 7 | 8 |
|---|---|---|---|---|---|---|---|---|---|
| Isophytol | [g] | 888 × 10³ | 296 | 445 | 296 | 296 | 296 | 296 | 296 |
| | [mole] | 3 × 10³ | 1 | 1.5 | 1 | 1 | 1 | 1 | 1 |
| HCOOH amount | [g] | 1.560 × 10³ | 520 | 780 | 520 | 520 | 520 | 460 | 154 |
| concentration | [% by weight] | 90 | 83.1 | 77.5 | 73.4 | 90 | 90 | 100 | 90 |
| amount | [mole] | 30.5 × 10³ | 9.4 | 13.1 | 8.3 | 10 | 10 | 10 | 3 |
| Reaction temperature | [°C.] | 60 | 60 | 60 | 60 | 60 | 40 | 108 | 60 |
| Reaction time | [h] | 2 | 8.5 | 30 | 40++ | 16 | 0.25 | 0.5 | 13++++ |
| Phytyl formate: | | | | | | | | | |
| Amount of crude product | [g] | 955 × 10³ | 307 | 470 | 311 | 301 | 303 | 314 | 300 |
| Purity of crude product | [% by weight] | 97.2 | 89.0 | 88.5 | 90 | 84.7 | 55 | 86.6 | 72 |
| Yield | [% of theory] | 98.2 | 84 | 85 | 86 | 79 | 51+++ | 84+++ | 67 |
| HCOOH+ | [g] | 1,425 × 10³ | 468 | 722 | 515 | 450 | 495 | 397 | 110 |
| Strength | [% by weight] | 83.1 | 77.8 | 73.4 | 68.4 | 83.5 | 84.5 | 94.3 | 75.6 |

+recovered HCOOH
++the experiment was stopped prematurely
+++Comparative Example; the remainder consists substantially of phytadiene
++++complete conversion of isophytol was not achieved

EXAMPLE 9

79 g (100 ml) of methanol and 1 g of sodium methylate were added to 317 g (0.95 mole) of a crude (97% pure) phytyl formate obtained according to Example 1. A mixture of methyl formate and methanol (81 g, ratio 3:1) was distilled from the reaction mixture through a 30 cm packed glass column under atmospheric pressure, until the boiling point had risen to 64° C. (reaction time 2 hours). The residue left consisted of 312 g of crude phytol which was distilled via a Claisen head. 283 g of a product which, according to analysis by gas chromatography (1 m Versamid-KOH, 250° C.) contained 79.3% of phytol, passed over at 135°–166° C./0.1 mbar. Accordingly, the yield was 79.8% of theory.

EXAMPLE 10

(a) Preparation of tetrahydrofarnesyl formate 113 g (0.5 mole) of tetrahydronerolidol (formula II, with n=1) and 260 g (5.1 moles) of 90% strength formic acid were reacted at 60° C. by a similar method to that of Example 1; the reaction time was 1.25 hours. 230 g of 82.6 percent strength by weight formic acid were recovered. The crude tetrahydrofarnesyl formate (formula I, with n=1) was distilled through a Claisen head. The yield was 113.1 g (corresponding to 90% of theory); boiling point=94°–96° C./0.1 mbar; $n_D^{25} = 1.4999$.

(b) Preparation of tetrahydrofarnesol 50 g (0.22 mole) of the tetrahydrofarnesyl formate obtained as described in 10 (a) were reacted with 39.5 g (50 ml) of methanol and 1 g of sodium methylate by a method similar to that of Example 9. The yield was 34.3 g (corresponding to 80% of theory) of tetrahydrofarnesol, boiling point 92° C./0.1 mbar; $n_D^{25} = 1.4578$ (physical data according to F. G. Fischer and K. Löwenberg, Annalen 475 (1929), 193: boiling point 152°–156° C./10 mbar; $n_D^{25} = 1.4562$).

EXAMPLE 11

(a) Preparation of
3,7,11,15,19-pentamethyl-2-eicosen-1-yl formate 275 g (0.75 mole) of 3,7,11,15,19-pentamethyl-1-eicosen-3-ol (formula II, with n=3) and 390 g (7.6 moles) of 90 percent strength by weight formic acid were reacted at 60° C. by a method similar to that of Example 1; the reaction time was 9 hours. 545 g of 85.8 percent strength by weight formic acid were recovered. The crude 3,7,11,15,19-pentamethyl-2-eicosen-1-yl formate was distilled through a Claisen head. The yield was 221 g (corresponding to 74.7% to 74.7% of theory); boiling point 176°–178° C./0.1 mbar; $n_D^{25} = 1.4582$.

(b) Preparation of
3,7,11,15,19-pentamethyl-2-eicosen-1-ol 152 g (0.39 mole) of 3,7,11,15,19-pentamethyl-2-eicosen-1-yl formate were reacted with 79 g (100 ml) of methanol and 2 g of sodium methylate by a method similar to that of Example 9. The yield was 86.6 g (corresponding to 61% of theory) of 3,7,11,15,19-pentamethyl-2-eicosen-1-ol, boiling point 177°–178° C./0.1 mbar; $n_D^{25} = 1.4647$.

EXAMPLE 12

(a) Preparation of dihydrogeranyl formate 312 g (2 moles) of 3,7-dimethyl-oct-1-en-3-ol (formula II, with n=0) and 1,040 g (20.3 moles) of 90 percent strength by weight formic acid were reacted at 30° C. by a method similar to that of Example 1; the reaction time was 1.5 hours. 912 g of 79.8 percent strength by weight formic acid were recovered. The crude dihydrogeranyl formate was freed from residual formic acid at 100° C./15 mbar. 329 g of 77.5 percent strength by weight formate were obtained. The yield was 69.5% of theory. (The pure product boiled at 86°–88° C./3.5 mbar, $n_D^{25} = 1.4431$; physical data according to British Pat. No. 765,516: boiling point 80° C./3 mbar, $n_D^{25} = 1.443$).

(b) Preparation of dihydrogeraniol 329 g (1.39 moles) of the 77.5 percent strength by weight dihydrogeranyl formate were reacted with 237 g (300 ml) of methanol and 5 g of sodium methylate by a method similar to that of Example 9. The yield was 219.2 g (corresponding to 67% of theory) of dihydrogeraniol of boiling point 70° C./0.2 mbar; $n_D^{25} = 1.4532$ (physical data according to British Pat. No. 765,516: boiling point 118°–119° C./20 mbar, $n_D^{25} = 1.4522$).

EXAMPLE 13

A mixture of 296 g (1 mole) of isophytol and 460 g (10 moles) of 100% strength formic acid was heated for 10 minutes at 100° C. 394 g of 94.6% strength formic acid were recovered as the lower phase. The product in the upper phase was subjected to incipient distillation, using a Claisen head, until the boiling point reached 29° C./15 mbar. The residue (279 g) contained about 34.4% of phytyl formate, according to titration and analysis by thin layer chromatography. This product was saponified with 79 g of methanol and 2 g of sodium methylate by a method similar to that of Example 9, and the crude product was distilled. 181 g of a mixture of boiling point 118°–119° C./0.1 mbar were obtained; according to analysis by gas chromatography, it contained 95% of phytadiene and 5% of phytol.

EXAMPLE 14

A mixture of 296 g (1 mole) of isophytol and 460 g (10 moles) of 100% strength formic acid was reacted for 34 hours at 5° C. by a method similar to that of Example 1. 351 g of 95% strength formic acid were recovered. The crude phytyl formate was subjected to incipient distillation, using a Claisen head, until the boiling point reached 32° C./15 mbar. 306 g of a product containing, according to titration, 89.2% of phytyl formate, were left as the residue. This product was reacted with 79 g of methanol and 2 g of sodium methylate by a method similar to that of Example 9. The yield was 197 g of a product of boiling point 136°–146° C./0.1 mbar, which according to analysis by gas chromatography contained 81.1% of phytol, 8.6% of isophytol and 9.3% of phytadiene.

EXAMPLE 15

Investigation, by thin layer chromatography, of the reaction of isophytol and formic acid in the molar ratio of 1:10.

A mixture of 1 mole of isophytol and 10 moles of formic acid of the particular concentration stated was heated at the stated reaction temperature and after the particular reaction time stated, a small sample of the reaction mixture was separated into its constituents by thin layer chromatography (Merck prepared silica gel plates; migrating agent: a 3:1 mixture of cyclohexane and ethyl acetate; spray developer: $KMnO_4$ in concentrated $H_2SO_4$), and the percentage by weight content of the constituents was estimated from the sizes of the spots.

(A) 70% strength aqueous formic acid
Reaction temperature: 100° C.

| Reaction time [min] | Isophytol | Phytyl formate [% by weight] | Phytadiene |
|---|---|---|---|
| 10 | 40 | 40 | 20 |
| 20 | 30 | 50 | 20 |
| 30 | 25 | 55 | 20 |
| 40 | 20 | 60 | 20 |
| 50 | 15 | 65 | 20 |
| 60 | 10 | 70 | 20 |
| 70 | 5 | 75 | 20 |
| 80 | 0 | 80 | 20 |

(B) 90% strength aqueous formic acid
Reaction temperature: 15° C.

| Reaction time [hours] | Isophytol | Phytyl formate [% by weight] | Phytadiene |
|---|---|---|---|
| 4 | 95 | 5 | 0 |
| 8 | 90 | 10 | 0 |
| 16 | 85 | 15 | 0 |
| 22 | 80 | 20 | 0 |
| 29 | 75 | 25 | 0 |
| 36 | 70 | 30 | 0 |
| 44 | 65 | 35 | 0 |
| 52 | 60 | 40 | 0 |
| 60 | 60 | 40 | 0 |
| 76 | 60 | 40 | 0 |

(C) 96% strength aqueous formic acid
Reaction temperature: 70° C.

| Reaction time [minutes] | Isophytol | Phytyl formate [% by weight] | Phytadiene |
|---|---|---|---|
| 10 | 0 | 95 | 5 |
| 20 | 0 | 95 | 5 |
| 30 | 0 | 95 | 5 |
| 40 | 0 | 95 | 5 |
| 50 | 0 | 90 | 10 |
| 60 | 0 | 90 | 10 |

(D) 96% strength aqueous formic acid
Reaction temperature: 80° C.

| Reaction time [minutes] | Isophytol | Phytyl formate [% by weight] | Phytadiene |
|---|---|---|---|
| 10 | 0 | 85 | 15 |
| 20 | 0 | 80 | 20 |
| 30 | 0 | 80 | 20 |
| 40 | 0 | 75 | 25 |
| 50 | 0 | 75 | 25 |
| 60 | 0 | 70 | 30 |

(E) 96% strength aqueous formic acid
Reaction temperature: 90° C.

| Reaction time [minutes] | Isophytol | Phytyl formate [% by weight] | Phytadiene |
|---|---|---|---|
| 10 | 0 | 80 | 20 |
| 20 | 0 | 70 | 30 |
| 30 | 0 | 60 | 40 |
| 40 | 0 | 50 | 50 |
| 50 | 0 | 45 | 55 |
| 60 | 0 | 40 | 60 |

(F) 100% strength formic acid
Reaction temperature: 70° C.

| Reaction time [minutes] | Isophytol | Phytyl formate [% by weight] | Phytadiene |
|---|---|---|---|
| 10 | 0 | 90 | 10 |
| 20 | 0 | 90 | 10 |
| 30 | 0 | 85 | 15 |
| 40 | 0 | 85 | 15 |
| 50 | 0 | 80 | 20 |
| 60 | 0 | 80 | 20 |

(G) 100% strength formic acid
Reaction temperature: 80° C.

| Reaction time [minutes] | Isophytol | Phytyl formate [% by weight] | Phytadiene |
|---|---|---|---|
| 10 | 0 | 85 | 15 |
| 20 | 0 | 80 | 20 |
| 30 | 0 | 70 | 30 |
| 40 | 0 | 60 | 40 |
| 50 | 0 | 50 | 50 |
| 60 | 0 | 50 | 50 |

(H) 100% strength formic acid
Reaction temperature: 90° C.

| Reaction time [minutes] | Isophytol | Phytyl formate [% by weight] | Phytadiene |
|---|---|---|---|
| 10 | 0 | 60 | 40 |
| 20 | 0 | 50 | 50 |
| 30 | 0 | 40 | 60 |
| 40 | 0 | 30 | 70 |
| 50 | 0 | 20 | 80 |
| 60 | 0 | 10 | 90 |

EXAMPLE 16 (COMPARATIVE EXAMPLE)

A mixture of 296 g (1 mole) of isophytol and 920 g (10 moles) of 50% strength aqueous formic acid was heated at 150° C. in a 3 liter autoclave. After the stated intervals, samples were taken from the reaction mixture and examined by thin layer chromatography, using a similar method to that of Example 15.

| Reaction time [hours] | Isophytol | Phytyl formate [% by weight] | Phytadiene |
|---|---|---|---|
| 1 | 70 | 15 | 15 |
| 6 | 30 | 30 | 40 |
| 11 | 5 | 25 | 70 |
| 13 | 0 | 25 | 75 |

We claim:
1. The process for the preparation of a terpenoid compound of the formula I

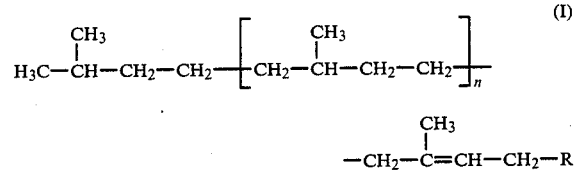

where R is —O—CO—H (Ia) and n is 2, wherein the corresponding tert.-vinylcarbinol of the formula II

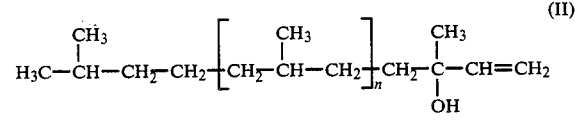

where n has the above meaning is reacted with about 10-fold molar excess, per mole of vinyl carbinol, of aqueous formic acid which is in the form of an aqueous solution of about 90 percent strength by weight, at from 55° to 65° C.

* * * * *